United States Patent
Peoples et al.

[11] Patent Number: 5,865,775
[45] Date of Patent: Feb. 2, 1999

[54] FOREARM SLEEVE DEVICE FOR ATTENUATING IMPACT-INDUCED SHOCK AND AMELIORATING THE EFFECT OF SAID SHOCK

[75] Inventors: Craig A. Peoples; Duane E. Peoples, both of Allentown; Glenn C. Westman, Bethlehem, all of Pa.

[73] Assignee: Polymer Dynamics Technology, Inc., Allentown, Pa.

[21] Appl. No.: 413,474

[22] Filed: Mar. 30, 1995

Related U.S. Application Data

[63] Continuation of Ser. No. 178,649, Jan. 7, 1994, abandoned, and a continuation of Ser. No. 867,766, Apr. 13, 1992, abandoned.

[51] Int. Cl.⁶ .................................................. A61F 5/10
[52] U.S. Cl. ............................. 602/20; 602/62; 602/63
[58] Field of Search ............................. 602/20, 21, 22, 602/62, 3, 63; 273/29 R, DIG. 15

[56] References Cited

U.S. PATENT DOCUMENTS

| | | | |
|---|---|---|---|
| 3,970,081 | 7/1976 | Applegate, Jr. | 273/29 R X |
| 4,832,010 | 5/1989 | Lerman | 602/63 |
| 5,063,913 | 11/1991 | Nyi | 602/20 |

*Primary Examiner*—Beverly M. Flanagan
*Attorney, Agent, or Firm*—David M. McConoughey

[57] ABSTRACT

The present invention provides a forearm-encircling sleeve for attenuating impact-induced shock and for ameliorating the effect of that shock on the elbow joint. The device made in accordance with the present invention provides energy-attenuating viscoelastic means that are positioned distally of the elbow joint and of the common tendon origins of the medial and lateral epicondyle heads of the humerus for attenuating impact-induced shock The energy-attenuating viscoelastic means are placed in force-receiving relationship with the forearm musculature responsible for extension and flexion of the wrist and, preferably, also that responsible for the extension and flexion of the fingers and the pronation and supination of the forearm. Means may be provided for applying a counterforce to these energy-attenuating viscoelastic means.

16 Claims, 11 Drawing Sheets

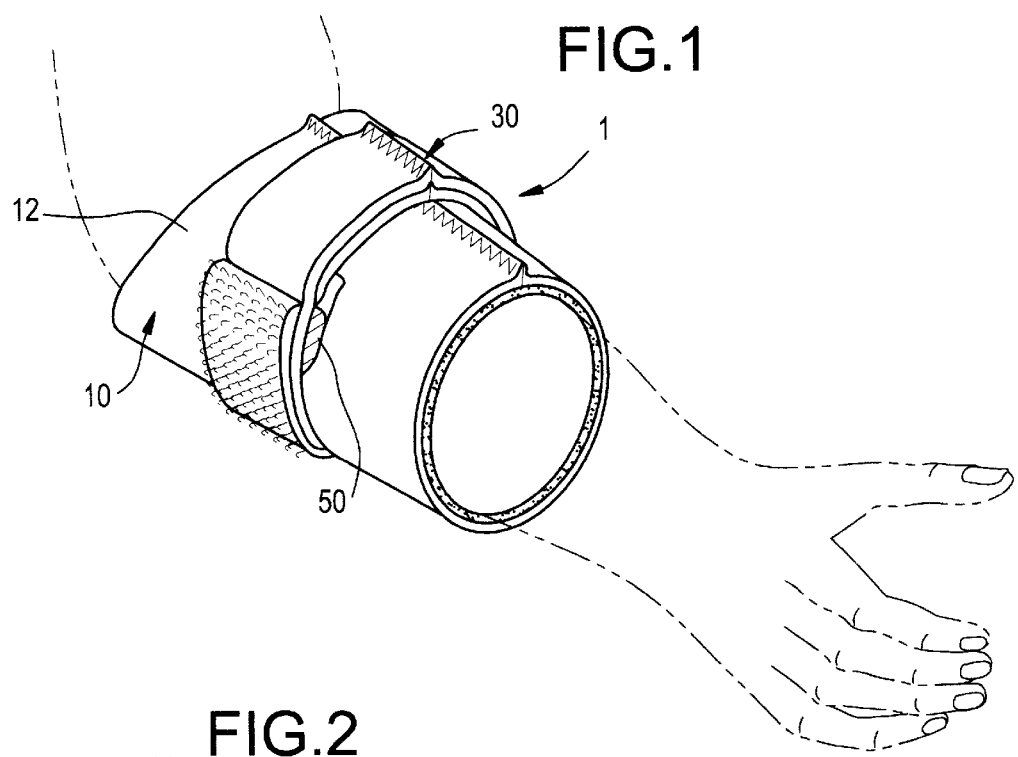
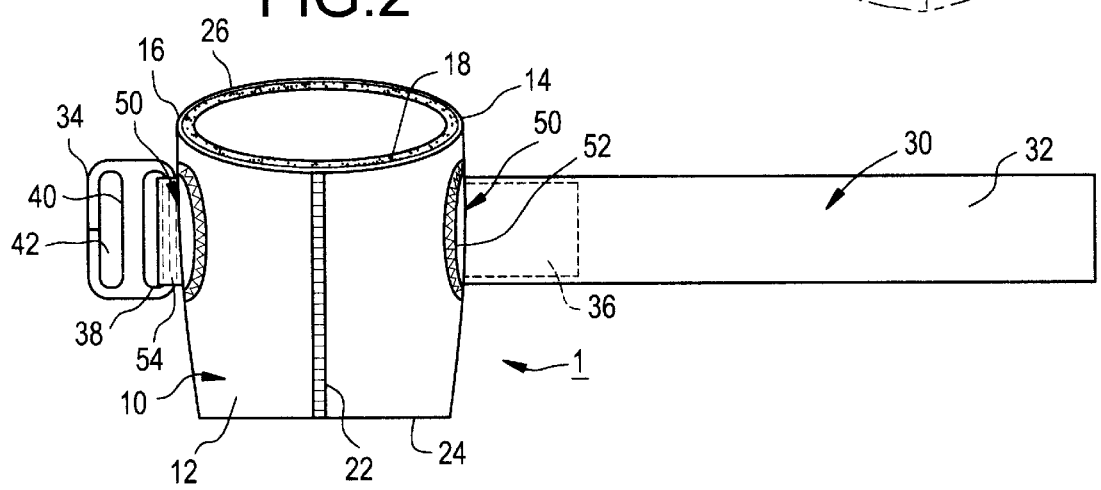
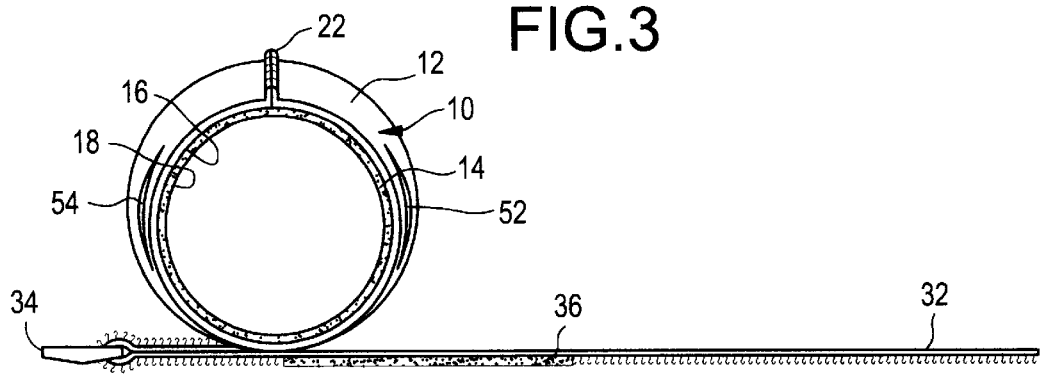

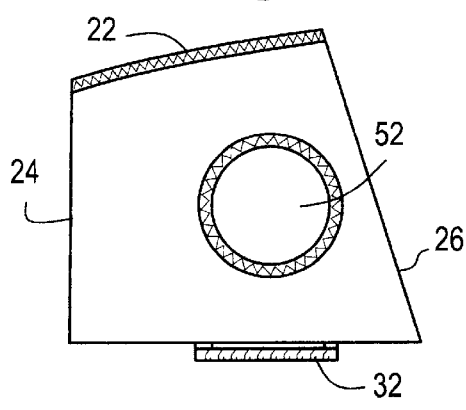
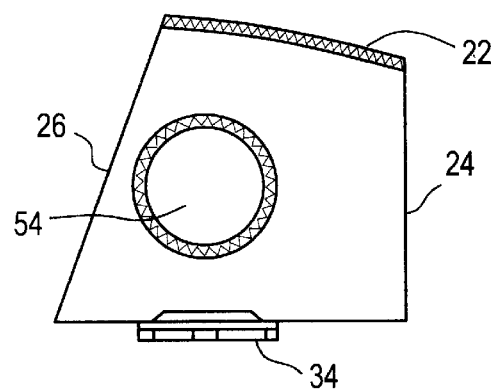
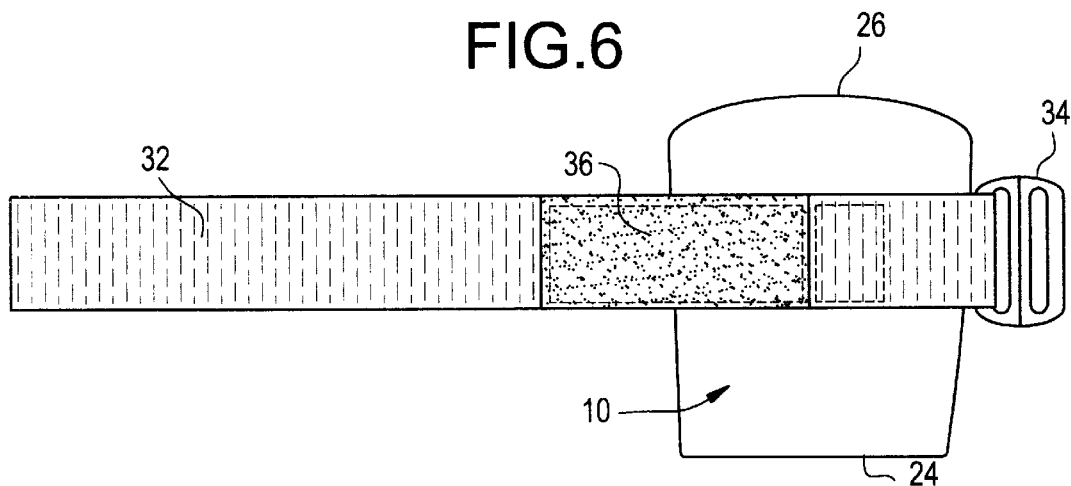
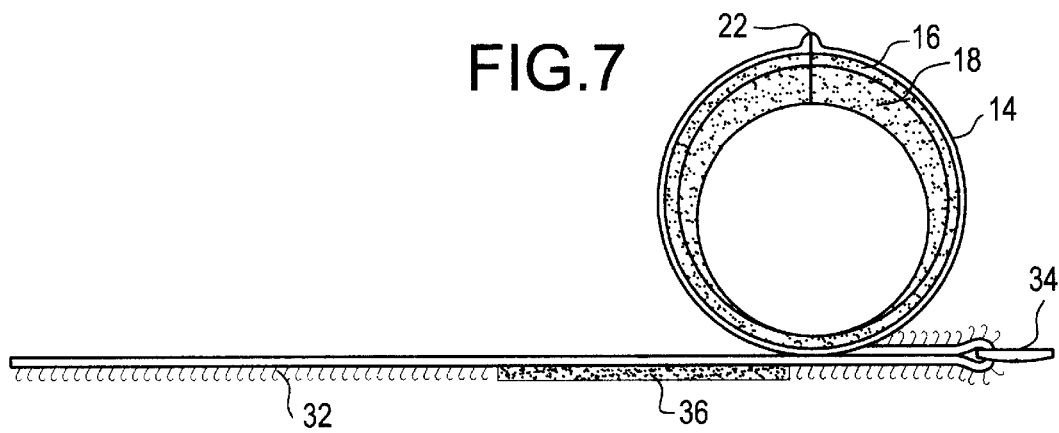

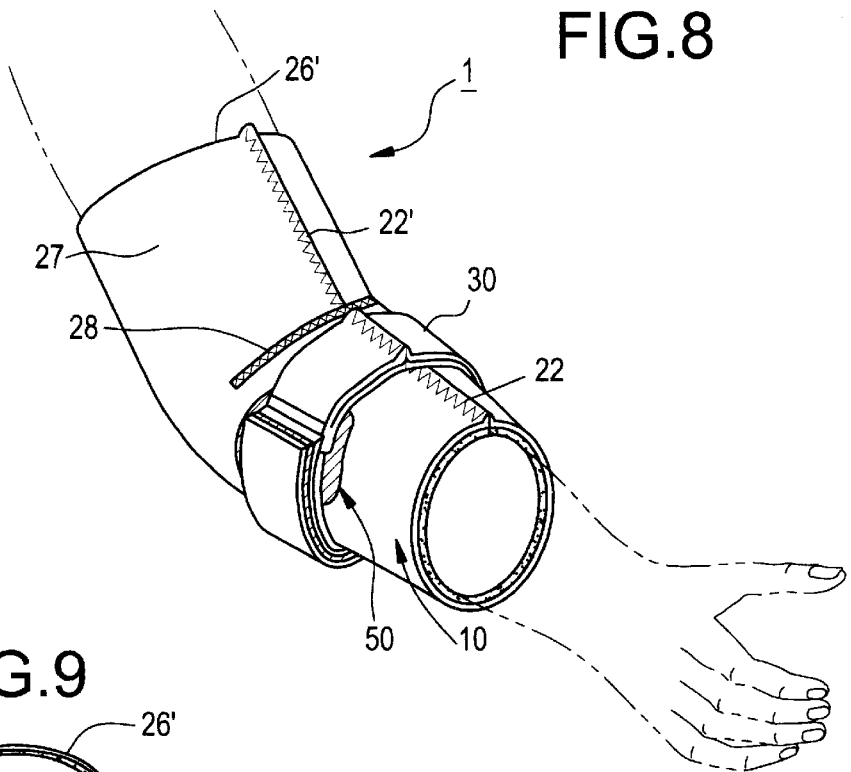
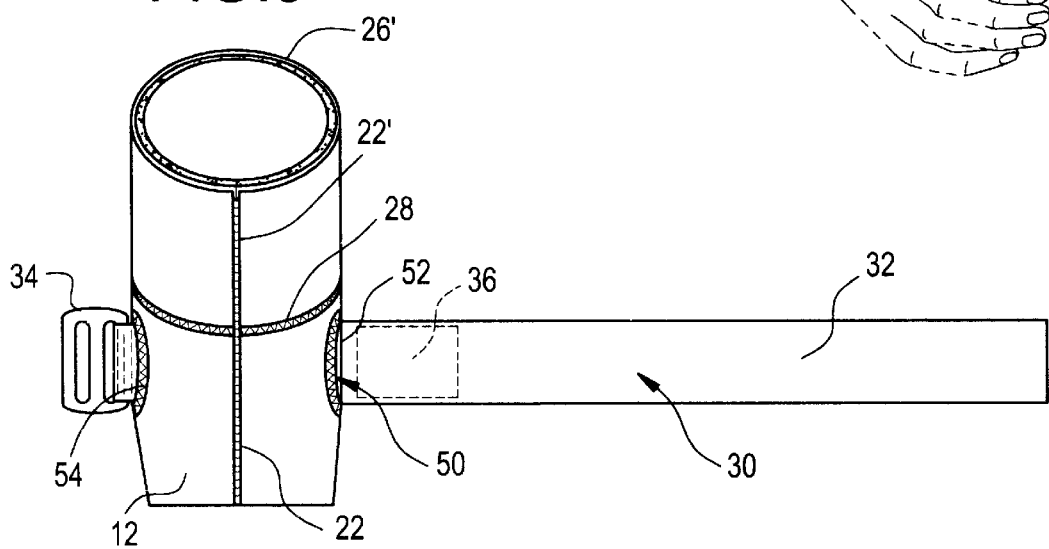
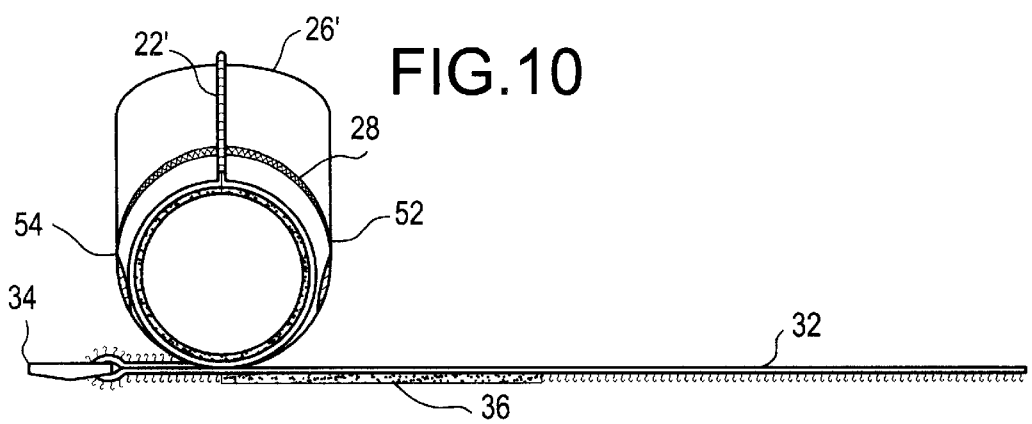

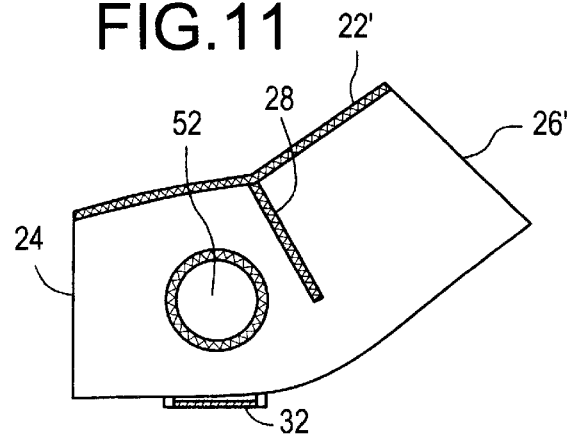
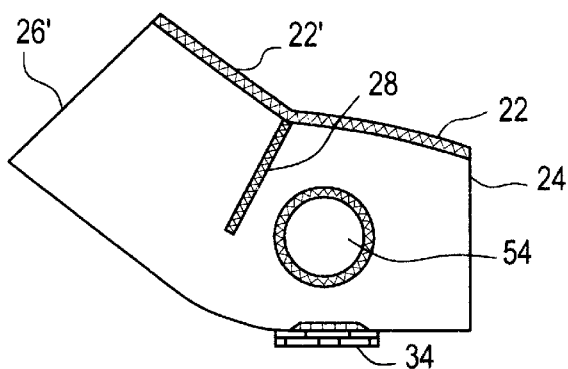
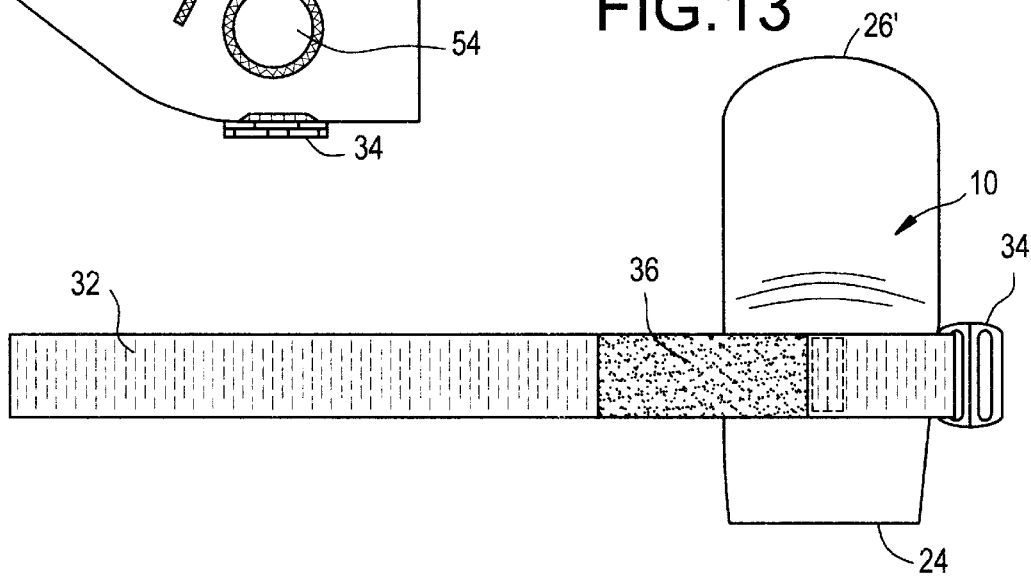
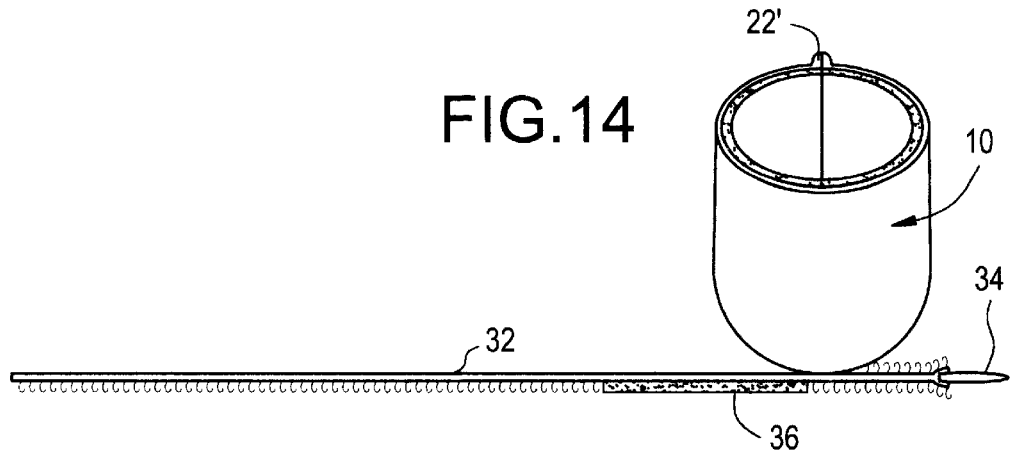

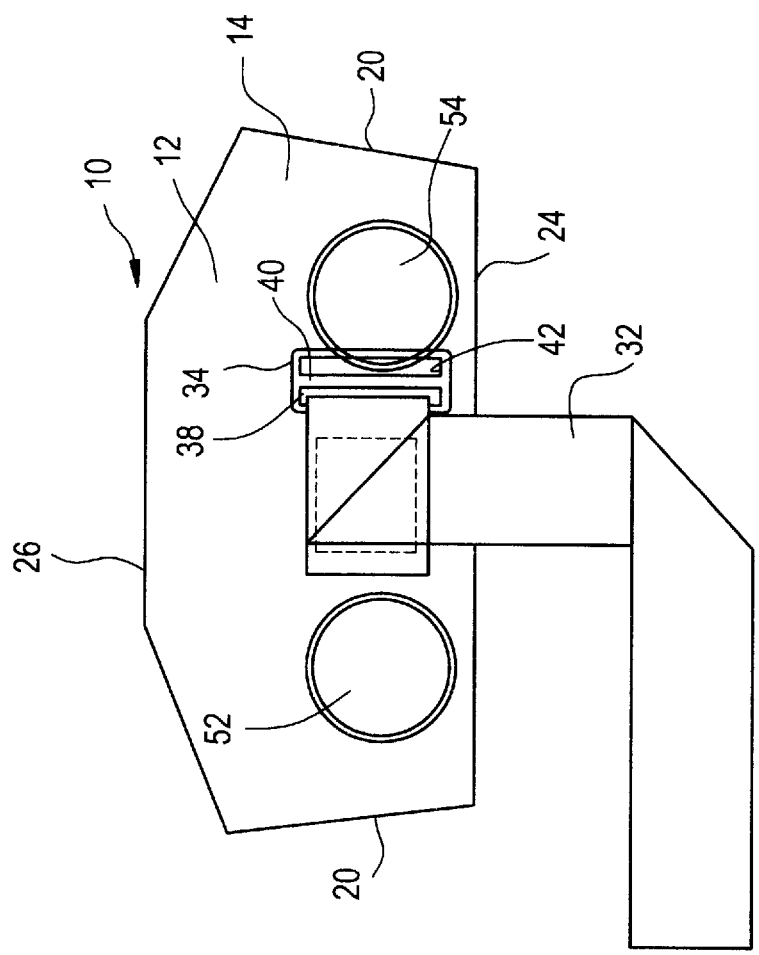

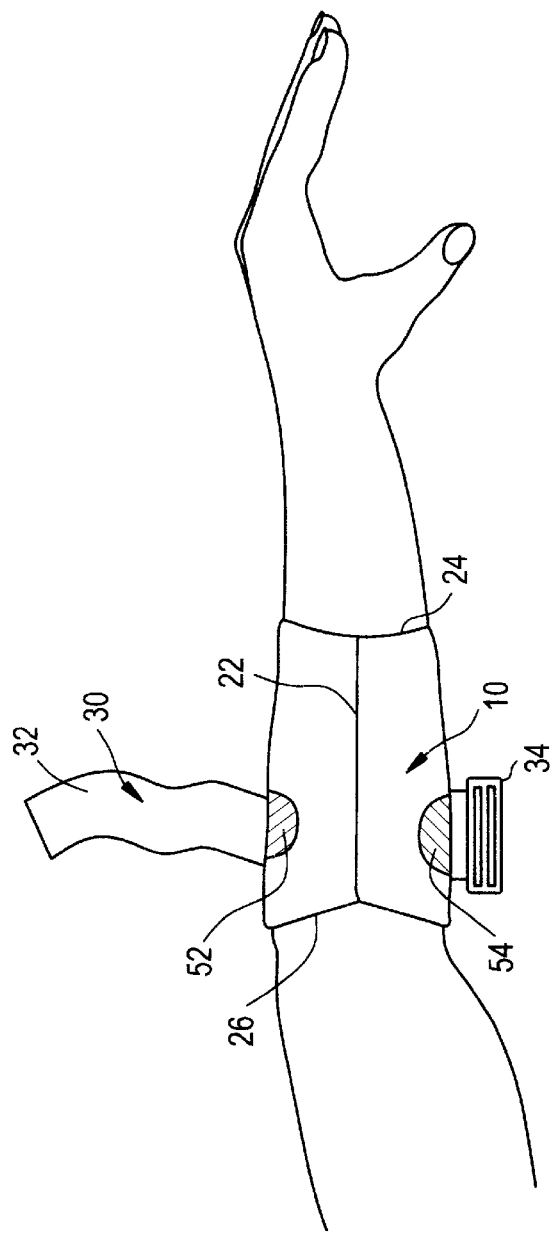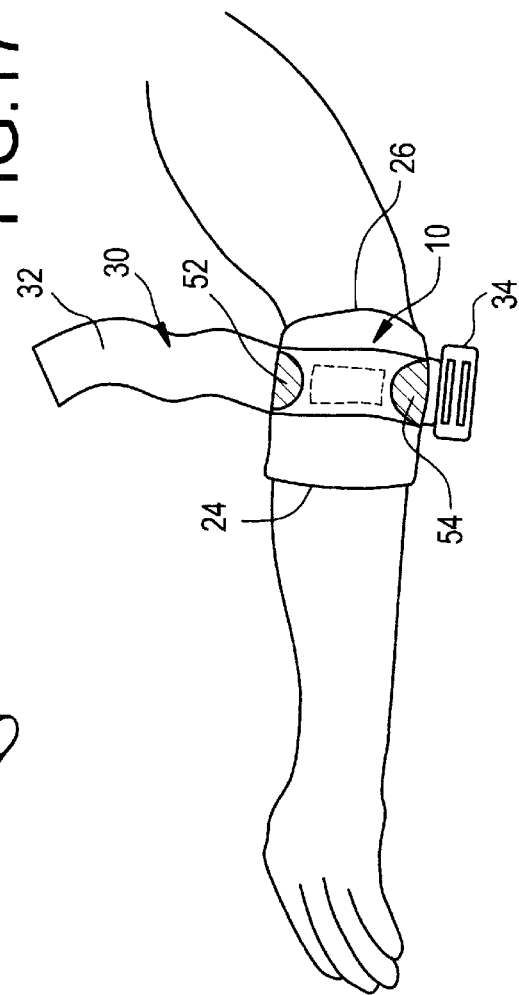

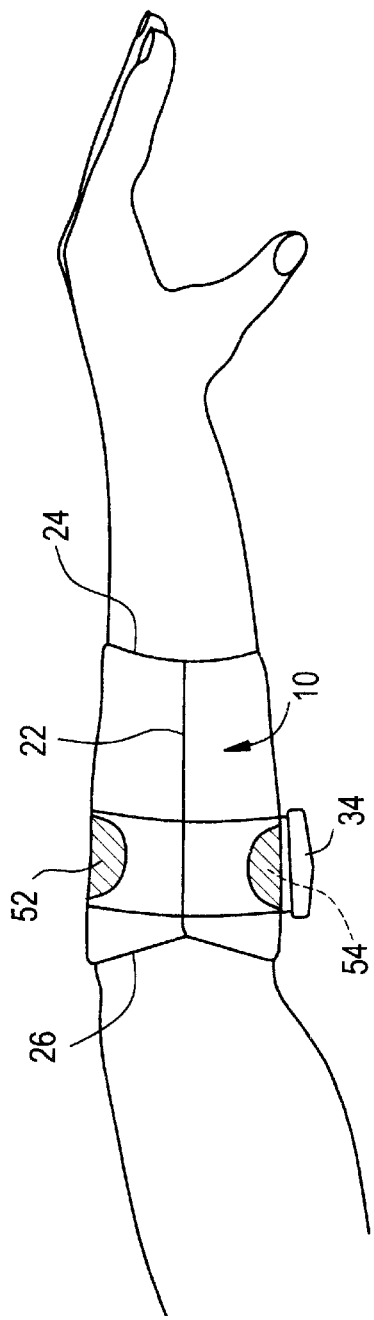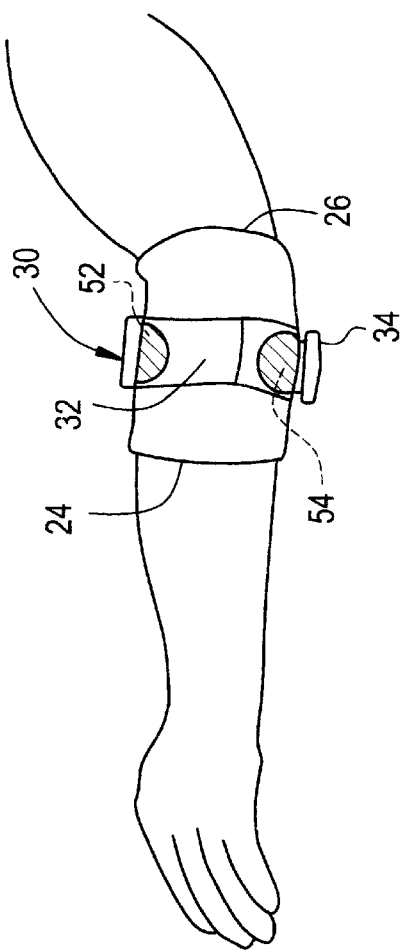

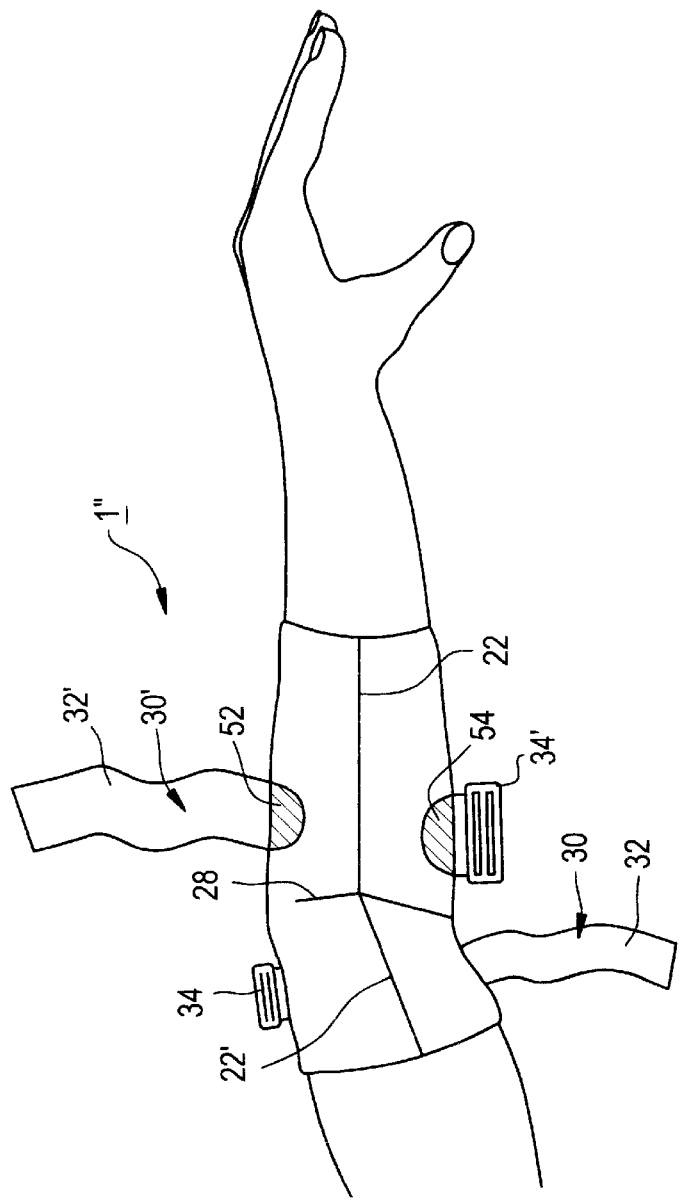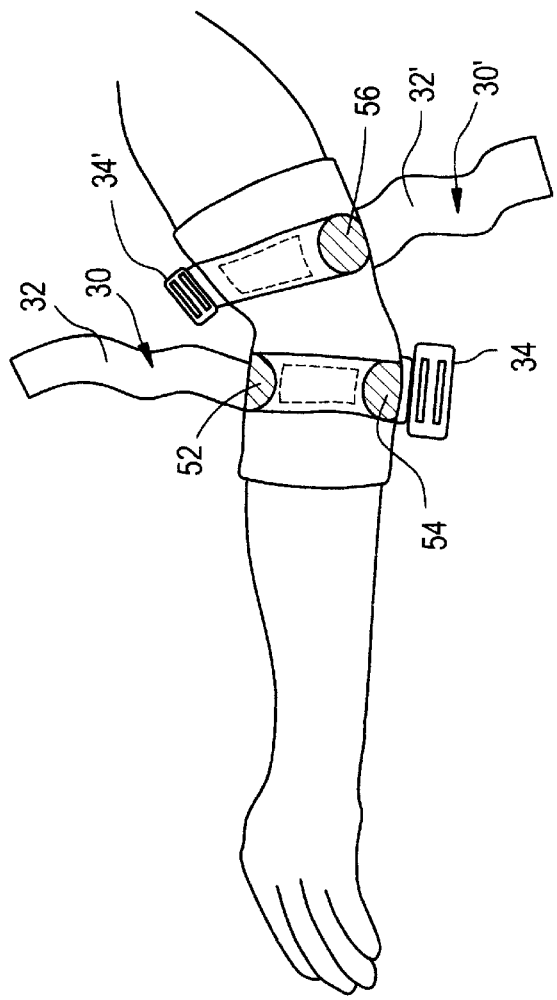

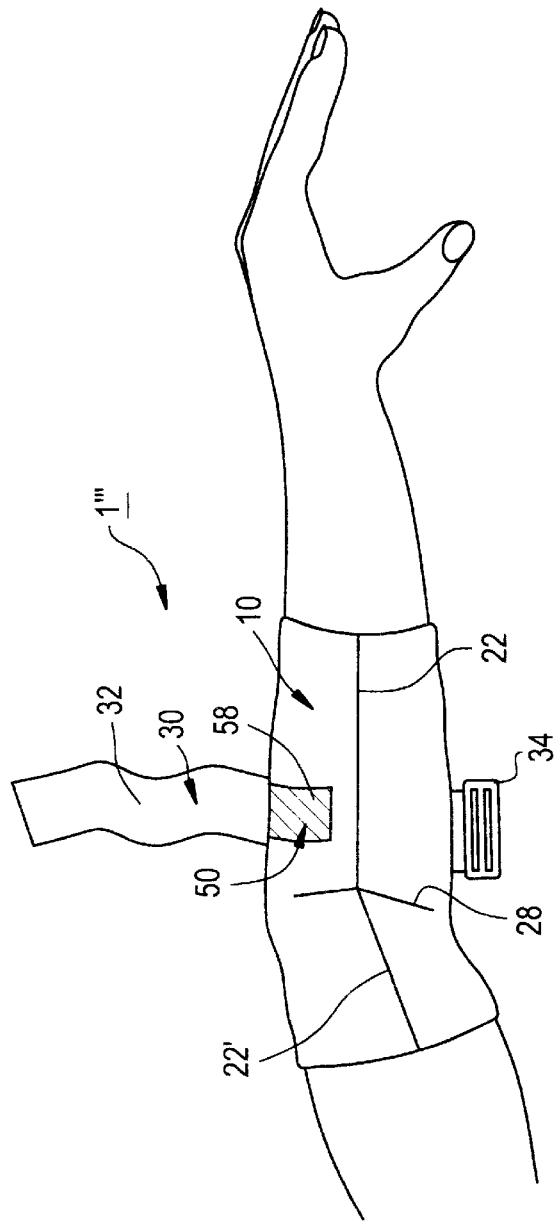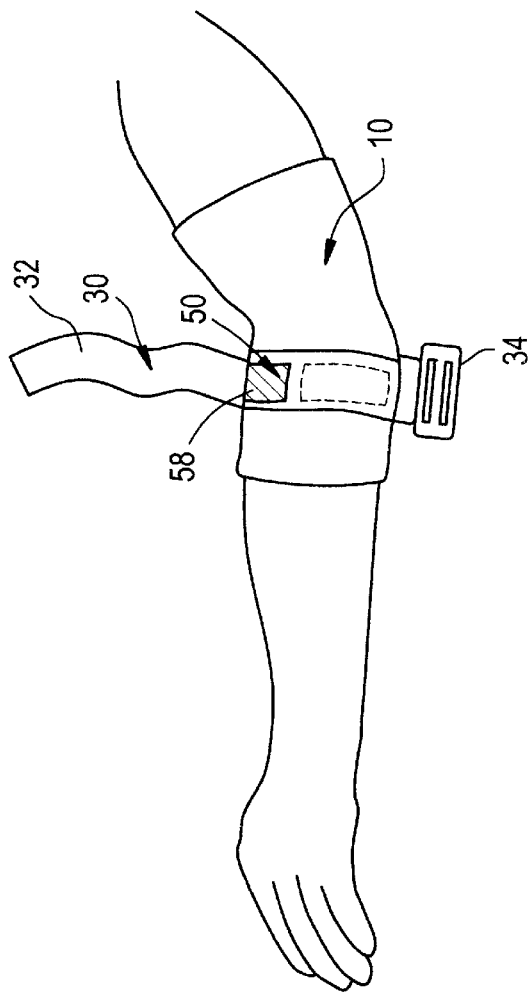

FOREARM SLEEVE DEVICE FOR ATTENUATING IMPACT-INDUCED SHOCK AND AMELIORATING THE EFFECT OF SAID SHOCK

CROSS-REFERENCE TO RELATED APPLICATION

This application is a continuation of application Ser. No. 08/178,649 filed Jan. 7, 1994 and a continuation of application Ser. No. 07/867,766 filed Apr. 13, 1992, both applications now abandoned.

BACKGROUND OF THE INVENTION

1. Field of the Invention

The present invention relates to a sleeve device for ameliorating the effect of impact-induced shock on the human elbow joint.

2. Description of the Related Art

A number of supports and braces have been proposed for the treatment of "tennis elbow" such as the application of restrictive pressure against expansion of the proximal forearm (U.S. Pat. No. 3,789,842), a fluid-filled pad (U.S. Pat. Nos. 4,905,997 and 4,905,998) or shock absorbing elements placed directly over the lateral and medial epicondyle of the humerus (U.S. Pat. No. 5,063,913). These approaches are inadequate to the task of attenuating impact-induced shock along the path that force is transmitted through the muscle-tendon complexes before that shock reaches the elbow joint.

SUMMARY OF THE PRESENT INVENTION

It is an object of the present invention to address stress to the musculo-skeletal system of the arm, particularly the elbow joint, during sporting and occupational activity, such as, for example, during backhand swing, forehand swing and service during the play of racquet sports.

It is an object of the present invention to provide a device that ameliorates the effect of impact-induced shock on the elbow joint.

The present invention provides a forearm-encircling sleeve device for attenuating impact-induced shock and for ameliorating the effect of that shock. The device comprises a sleeve member and energy-attenuating viscoelastic means for attenuating impact-induced shock, said sleeve member positioning said energy-attenuating viscoelastic means distal to the elbow joint and to the common tendon origins of the medial and the lateral epicondyle heads of the humerus and in force-receiving relationship with forearm musculature responsible for flexion and extension of the wrist.

BRIEF DESCRIPTION OF THE DRAWINGS

FIG. 1 is a perspective view of a first embodiment of a forearm sleeve device made in accordance with the present invention in position on the right forearm of a user with the fastening member secured and showing the user's arm in phantom.

FIG. 2 is top plan view of the embodiment of FIG. 1 with the fastening member open and unsecured.

FIG. 3 is a front elevation view of the device of FIG. 2.

FIG. 4 is a side elevation view of the device of FIG. 2 viewed from the right side of FIG. 2.

FIG. 5 is a side elevation view of the device of FIG. 2 viewed from the left side of FIG. 2.

FIG. 6 is a bottom plan view of the device of FIG. 2.

FIG. 7 is a rear elevation view of the device of FIG. 2.

FIG. 8 is a perspective view of a second embodiment of a forearm sleeve device made in accordance with the present invention in position on the right forearm of a user with the fastening member secured and showing the user's arm in phantom.

FIG. 9 is a top plan view of the device shown in FIG. 8.

FIG. 10 is a front elevation view of the device of FIG. 9.

FIG. 11 is a side elevation view of the device of FIG. 9 as viewed from the right side in FIG. 9.

FIG. 12 is a side elevation view of the device of FIG. 9 viewed from the left side of FIG. 9.

FIG. 13 is a bottom plan view of the device of FIG. 9.

FIG. 14 is a rear elevation view of the device of FIG. 9.

FIG. 15 is a top plan view of a partially assembled device of the embodiment of FIGS. 1–7.

FIG. 16 is a top view of the embodiment of FIGS. 1–7 in position on the left forearm of a user showing the position of the device and the energy-attenuating, viscoelastic means with respect to the forearm and with the fastening member not secured.

FIG. 17 is a side view of the device of FIGS. 1–7 positioned in accordance with FIG. 16.

FIG. 19 is a top view of the embodiment of FIGS. 1–7 in positioned on the left forearm of a user showing the position of the device and the energy-attenuating, viscoelastic means with respect to the forearm and with the fastening member secured.

FIG. 20 is a side view of the device of FIGS. 1–7 positioned in accordance with FIG. 19.

FIG. 22 is a top view of a third embodiment of a forearm sleeve device made in accordance with the present invention positioned on the left forearm and upper arm of a user showing the position of the device and the energy attenuating, viscoelastic means with respect to the forearm and with the fastening members unsecured.

FIG. 23 is a side view of the device of FIG. 22 positioned in accordance with FIG. 22.

FIG. 24 is a top view of a fourth embodiment of a forearm sleeve device made in accordance with the present invention positioned on the left forearm and upper arm of a user showing the position of the device and the energy attenuating, viscoelastic means with respect to the forearm and with the fastening member unsecured.

FIG. 25 is a side view of the device of FIG. 24 positioned in accordance with FIG. 24.

DESCRIPTION OF VARIOUS EMBODIMENTS OF THE INVENTION

Figure 18:
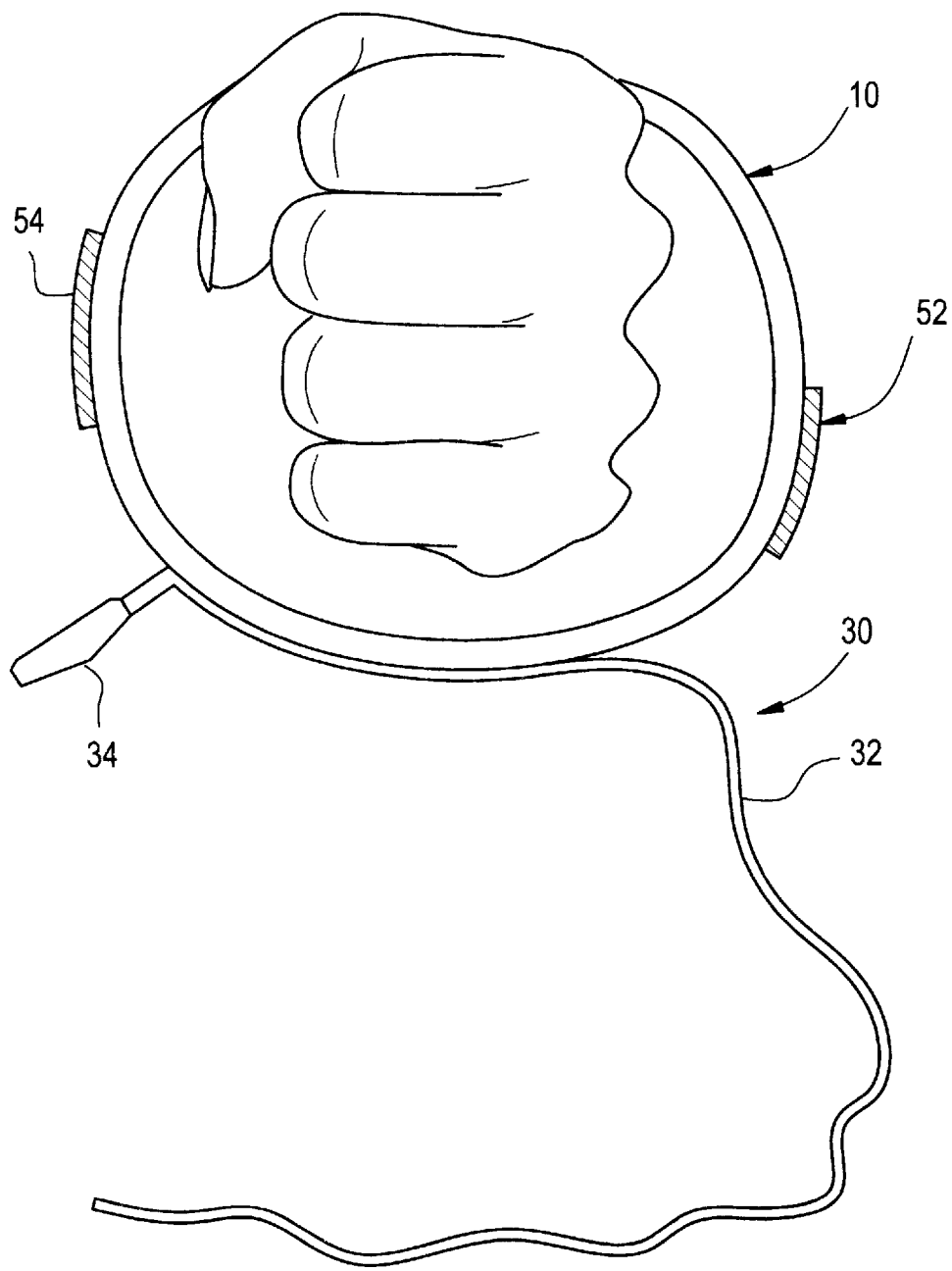
FIG. 18 is a front view of the device of FIGS. 1–7 positioned in accordance with FIG. 16.

The present invention provides a forearm-encircling sleeve for attenuating impact-induced shock and for ameliorating the effect of that shock on the elbow joint. The device made in accordance with the present invention provides energy-attenuating viscoelastic means that are positioned distally of the elbow joint and of the common tendon origins of the medial and lateral epicondyle heads of the humerus for attenuating impact-induced shock. The energy-attenuating viscoelastic means are placed in force-receiving relationship with the forearm musculature responsible for extension and flexion of the wrist and, preferably, also that responsible for the extension and flexion of the fingers and the pronation and supination of the forearm. Means may be provided for applying a counterforce to these energy-attenuating viscoelastic means.

The forearm sleeve device 1 (FIGS. 1–25) made in accordance with the present invention comprises a flexible sleeve member 10, energy-attenuating, viscoelastic means 50 for attenuating impact-induced shock and a fastening member 30.

Sleeve member 10 is comprised of a laminate sheet member 12 (FIG. 15) that, in a preferred embodiment, is comprised of three layers - an outer cover 14, a heat-insulative core layer 16 and an inner liner 18. The opposed side edges 20 (FIG. 15) of laminate 12 are joined by a stitched seam 22 (FIGS. 2–5 and 1) to form a tube in which the inner liner 18 provides its inner surface and cover 14 provides its outer surface. While the sleeve member 10 has a generally frusto-conical tubular configuration, it should be borne in mind that the sleeve is a conical section in which the front edge 24 (FIG. 2) of the sleeve defines a front opening whose general plane is generally perpendicular with respect to the longitudinal central axis of the conical section and in which the rear edge 26 (FIG. 2) of the sleeve defines a rear opening whose general plane is inclined with respect to the longitudinal central axis of the conical section. This configuration of the rear opening permits the sleeve member 10 to overly more of the posterior of the forearm and elbow. Cover 14 and inner liner 18 are constructed of preferably biaxially elastically extensible fabric. Core 16 is also elastically extensible. Core 16 is preferably a heatinsulative closed cell elastomer foam, more preferably a nitrogen-blown synthetic rubber foam, such as NEOPRENE synthetic rubber. The opposed edges of laminate sheet 12 are joined together by stitching, preferably by blind stitch and coverstitch, to form the seam 22. This seam 22 provides a visual reference for rotationally aligning the device 1 on the forearm of the user. The desired technique of stitching may be the combination of a blind stitch and coverstitch. In application, a blind stitch ensures the constant uniformity of stitch depth and needle penetration, more specifically, a blind stitch does not penetrate the inner membrane of the sleeve sheet member 12. In so doing, the structural integrity of the sleeve membrane is not compromised during this important stage of construction. A coverstitch effectively locks two opposing stitches together. The interlocking of opposing stitches minimizes the possibility of a single torn stitch unwraveling the remaining stitches.

Energy-attenuating viscoelastic means 50 are affixed to sleeve member 10 in specific locations so that such means are positioned in force-receiving relationship with respect to the musculature of the forearm that is responsible for certain movements of the forearm, wrist and fingers. Preferably, the energy-attenuating viscoelastic means comprises a viscoelastic elastomeric solid polymer material such as a viscoelastic polyurethane elastomer, examples of which are disclosed in U.S. Pat. Nos. 4,722,946; 4,876,805 and 4,980, 386, the disclosure of each of which is incorporated herein by reference. In the embodiment shown in FIGS. 1–15, the energy-attenuating means 50 comprise two viscoelastic elastomer pads 52 and 54 affixed to the outer surface of sleeve member 10. These pads 52 and 54 are configured as flat disks and dimensioned, preferrably, at about two (2) inches in diameter.

Fastening means 30 is comprised of a strap member 32 and a buckle 34. In order to facilitate easy opening, closing and adjustment, strap member 32 is provided with hook fabric on its external surface (the bottom surface as shown in FIGS. 3, 6 and 7.) This hook fabric interacts with a loop fabric sheet 36 (FIG. 3, 6 and 7) affixed to the outer surface of the strap member 32. The fastening means 30 is secured by passing the strap 32 over the top (seam side) of the sleeve member 10 and passing the end of the strap 32 through the proximal opening 38 in buckle 34, around a central spindle 40 in the buckle 34 and then through distal opening 42. The strap member 32 is then drawn tight to the desired tension to apply the desired counterforce to the energy-attenuating viscoelastic means 50 (pads 52 and 54) and secured in place by pressing the hook fabric of strap 32 against the loop fabric of sheet 36.

The posterior edge of sleeve member 10 serves to locate the forearm sleeve device 1 on the forearm of the user by the abutment of rear edge 26 in the crease of the elbow joint. Seam 22 serves as a visual reference for alignment of the device 1 rotationally on the forearm in that the longitudinal central axis of the seam 22 should be aligned with the cleft between the thumb and fingers of the hand when the user's hand is facing palm inward and thumb upward as in FIGS. 1, 8, 16, 19, 22 and 24.

Based on the foregoing orientation of the sleeve device 1 when it is applied to the user, the position of the energy-attenuating viscoelastic means 50, e.g., each viscoelastic pad 52 and 54, is fixed so that each pad is positioned to overly forearm musculature responsible for specific movements of the forearm, wrist or fingers. For example, in a preferred embodiment of the present invention a first impact energy-attenuating viscoelastic pad 52 is disposed on the sleeve member 10 in force-receiving relationship with the forearm musculature responsible for flexion of the wrist and in a position distal to the common flexor tendon origin of the medial epicondyle head of the humerus and a second impact energy attenuating viscoelastic pad 54 is positioned in force-receiving relationship with the forearm musculature responsible for extension of the wrist and in a position distal to the common extensor tendon origin of the lateral epicondyle of the humerus.

The fastening means 30 provide, inter alia, a means for applying a counterforce to the impact energy-attenuating viscoelastic means 50. Since the zone of attachment of the strap member 32 is positioned on the sleeve member 10 so that strap member 32 overlies each impact energy-attenuating viscoelastic pad 52 and 54, tensioning the strap member 32 appliers a radially inward force on the outer surface of each viscoelastic pad. This acts as a counterforce to any force directed radially outwardly.

The sleeve member 10 contributes three functions to the forearm sleeve device 1. First, it serves to position and orient the energy-attenuating viscoelastic means 50 with respect to the forearm so as to interact with the forearm in effective force-receiving relationship in order to attenuate impact-induced shock and ameliorate its effect. Second, it applies a pressure to the forearm that is directed radially inwardly (even when fastening means 30 is not tightened.) Third, it serves to retain heat in the forearm in the region that it covers.

Since the sleeve device 1 is intended to attenuate impact-induced shock and ameliorate its effects at the level of the elbow joint, the energy-attenuating viscoelastic means, e.g. pads 52 and 52, are positioned with respect to the functional anatomy of the elbow joint so as to attenuate that shock before it reaches the elbow joint.

It has been found that a muscle-tendon complex in which the muscle is contracted is relatively rigid and transmits impact-induced shock more readily than when the muscle is relaxed. Consequently, for example, the single impact of a ball against a racquet that is firmly grasped is transmitted well beyond the hand. Further, as another example, the multiple shocks of a vibratory tool gripped by the hand is also transmitted well beyond the hand. In addition, the contraction of the muscle itself places the muscle-tendon complex under stress rendering it more susceptible to the shock(s).

As it relates to the elbow joint, supination of the forearm contracts the supinator (that has an origin on the lateral epicondyle of the humerus) and pronation contracts the pronator teres (that has an origin on the medial epicondyle of the humerus). Consequently, impacts during supination or pronation or when the forearm is tensed against impact result in the transfer of shock across the elbow joint through the contracted supinator or pronator teres muscle-tendon complexes as the case may be. Further, flexion of the wrist contracts the flexor carpi radialis, palmaris longus and flexor carpi ulnaris (that have their origin on the medial epicondyle through the common flexor tendon) and extension contracts the extensor carpi ulnaris and extensor carmi radialis brevis (that each have their origin on the lateral epicondyle through the common extensor tendon) and the extensor carpi radialis longus (that has its origin further up on the humerus than the lateral epicondyle.) Consequently, impacts during contraction of the flexors and/or extensors of the wrist, such as flexion, extension or maintaining a wrist position against impact, result in the transfer of shock across the elbow joint through the common flexor tendon or the common extensor tendon and the extensor carpi radialis longus, as the case may be. Also, flexion of the fingers contract the flexor digitorum superficialis (that has an origin through the common flexor tendon on the medial epicondyle) and extension of the fingers contracts the extensor digitorum and extensor digiti minimi (that each have an origin through the common extensor tendon on the lateral epicondyle.) Consequently, impacts during contraction of the flexors and/or extensors of the fingers result in the transfer of shock across the elbow joint through the common flexor and/or extensor tendons. Consequently, it becomes apparent that activities involving concurrent (1) impact and (2) flexon and/or extension of the wrist and fingers and supination and/or pronation of the forearm, such as racquet sports, produce shock transfer through the relevant muscle-tendon complexes to the elbow joint.

The present invention places shock energy-attenuating viscoelastic elastomer pads upstream of the elbow joint in this shock transfer path, i.e, distally of the lateral and medial epicondyles and of the elbow joint. This serves at least partially to isolate the elbow joint from impact-induced shock transferred through the muscle-tendon complexes. Further, the energy-attenuating viscoelastic elastomer pads are positioned in force-receiving relationship to the common extensor and flexor tendons and their associated muscles in the vicinity of the junction between those tendons and their associated muscles. The viscoelastic pads absorb both surface (epidermal) and internal (muscle) shock and vibration.

Observation of the service of a tennis ball or the manual use of a screwdriver, for example, indicates that extreme levels of pronation and/or supination of the forearm are potential causes for insult to the tendons of the forearm and upper arm. Pronation may cause the common extensor tendon of the extensor carpi radialis brevis, extensor comunus digitorum and other relevant surrounding muscles to stretch over the radial head of the humerus. Supination may cause stretching of the flexor carpi ulnarus, flexor carpi radialis and palmaris longus that share a common flexor tendon origin to the medial epicondyle of the humerus.

The force-receiving relationship of the viscoelastic pads is achieved by the direct application of pressure directed radially inwardly over the viscoelastic pad. Such pressure is applied through the use of strap member 32. By accurately applying pressure to the muscle groups responsible for the flexion and extension of the wrist and fingers and for the supination and pronation of the forearm, stress is relieved from the tendons connecting the radius and ulna to the lateral and medial humeral epicondyles and the energy of impact-induced shock is attenuated by the viscoelastic properties of the viscoelastic means 50. The strap member 32 permits easy adjustment of pressure during the course of use, such as when the user warms up and the forearm muscles become engorged. This pressure is of two types—restrictive and compressive. Restrictive pressure acts as a counterforce during brief periods of muscle contraction, namely upon impact (and its induced shock). Compressive pressure is a constant pressure which is applied to relieve the stress that has been placed on the tendons of common origin, e.g., the common extensor and flexor tendons. Pneumoplesmagraphic studies indicate that the sleeve member 10, per se, should apply an intrinsic pressure sufficient to produce the onset of restriction of venous blood in the forearm. This is achieved by the elasticity of the sleeve member 10 and appropriate sizing. The use of a viscoelastic elastomer pad permits the viscoelastic elastomer to function as a force transfer member for the foregoing pressure. In this role the viscoelastic insert acts as a buffer to allow the temporary expansion of contracted muscles while retaining a generally compressive pressure. In other words, since each pad is viscoelastic, (i.e., it has some of the characteristics of a liquid (although it is solid) in that it yields deformably under stress) the insert will temporarily deform under the temporary expansion of the muscles contracting and return to its original configuration when such stress is released. More importantly the energy-attenuating viscoelastic means 50, e.g. pads 52 and 54, act to directly attenuate the energy of the impact-induced shock as it is transmitted up the arm of the user. This attenuation occurs before the shock reaches the elbow joint.

Heat retention by the sleeve member 10 in the region of the forearm that it overlies serves many purposes. This retained heat increases circulation in that region of the forearm, which in turn, is believed to exhibit a healing effect on minor injuries. Further, heat retention places the muscles, tendons and ligaments affected by the heat retention in a more elastic condition, rendering them subsequently less susceptible to stress-induced strain and tearing. Much like a rubber band, muscles, tendons and ligaments are more easily damaged when they are in a cold condition, yet become more flexible on warming. Another benefit of heat retention and increased temperature within the affected region is that the sensation of pain travels along the same nerve synapses as does heat and the sensation of heat overrides that of pain, effectively masking minor discomfort. The sleeve member 10 provides heat retention facilitating the warming up of muscles, tendons and ligaments and also provides the retention of heat during activity so as to maintain the muscles, tendons and ligaments in a warm condition.

Figure 21:
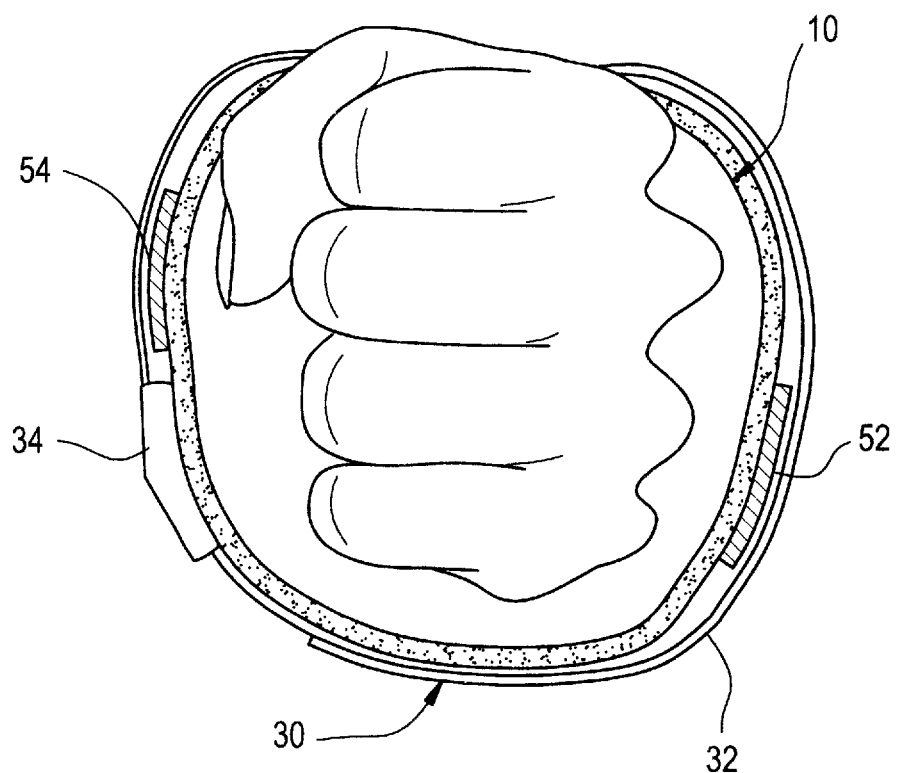
FIG. 21 is a front view of the device of FIGS. 1–7 positioned in accordance with FIG. 19.

FIGS. 16–21 illustrate the application of the sleeve device 1 of FIGS. 1 through 7 to the left forearm of a user. In FIGS. 16, 17 and 18 the device 1 has been applied to the left forearm with the first viscoelastic pad 52 placed distally of the lateral epicondyle and the elbow joint and in overlying relation to the relevant musculature on the forearm at its juncture with the common extensor tendon and the second viscoelastic pad 54 placed distally of the medial epicondyle and the elbow joint and in overlying relation to the relevant musculature on the forearm at its juncture with the common flexor tendon. The elasticity of the sleeve member 10 applies gentle pressure to the region of the forearm that it overlies. In FIGS. 19, 20 and 21, the strap member 32 has been threaded through the buckle 34, drawn tight and the hook and loop fabric interlocked so that additional pressure has been applied to sleeve member 10 and a counterforce has been applied to viscoelastic pads 52 and 54.

In a second preferred embodiment (FIGS. 8–14) of a forearm-encircling sleeve device 1' made in accordance with the present invention, the device 1 is modified from the embodiment of FIGS. 1 through 8 and 15 by extending the laminate sheet member 12 rearwardly to form a tubular extension member 27 whose longitudinal central axis is angled obliquely upward with respect to the longitudinal central axis of the lower part of the sleeve member 10. The extension member 27 has a generally frusto-conical tubular configuration in which the rear edge 26' defines a rear opening whose general plane is perpendicular to the longitudinal central axis of the conical section and in which the general plane of the juncture between the extension member 27 and the remainder of the sleeve member 10 is inclined with respect to the longitudinal central axis of the conical The opposed sides of the laminate sheet member 12 are joined by stitching, as aforesaid, so that seam 22 extends up the extension member 27 and upper arm as seam 22'. The extension member 27 is joined to the remainder of the sleeve member 10 by a dart 28 on the anterior or top portion of the sleeve device 1 so that dart 28 fits into the crook of the elbow joint. Dart 28 is stitched together in the same manner as seams 22 and 22'. The dart 28 is configured to minimize bunching of the sheet member 12 during flexion of the forearm. The sleeve device 1' of the embodiment of FIGS. 8–14 is particularly useful for industrial usage where some restriction in the flexion and extension of the elbow joint is permissible and even desirable. The ability to comfortably participate in a given activity while wearing a sleeve device is a major design concern. Acceptance of a prophylactic or therapeutic device, such as the device made in accordance with the present invention, depends heavily upon it not interfering with the normal range of motion. To address this concern, the embodiments of FIGS. 8–14, 22 & 23 and 24 & 25 are designed to follow the normal bend of the elbow joint. Casual observation of the relaxed arm position indicates the desired bend of an encircling device. The correct placement of darts effectively minimizes bunching of excess fabric that might be common to undarted cylindrical or conical sleeve constructions.

In a third preferred embodiment (FIGS. 22 and 23) of a forearm-encircling sleeve device 1" made in accordance with the present invention, the device 1" is modified from the embodiment of FIGS. 8–14 by providing further energy-attenuating viscoelastic means 50 in the form of a third viscoelastic elastomer pad 56 that is positioned in force-receiving relationship with the insertion tendon of the triceps brachii muscle of the upper arm and in a position proximal to the elbow joint. A second fastening means 30' comprising a strap member 32' and buckle 34' provide the same function as the aforesaid fastening means 30 of FIGS. 1–7. The viscoelastic elastomer pad 56 provides impact-induced shock attenuation to the triceps brachii muscle and associated muscles of the upper arm and provides the functionality as aforesaid for viscoelastic elastomer pads 52 and 54. The sleeve device 1", as with the sleeve device 1' of the embodiment of FIGS. 8–14, is particularly useful for industrial usage where some restriction of flexion and extension of the elbow joint is desirable. The embodiment FIGS. 22 and 23 represents an alternate embodiment which addresses all three areas of potential elbow discomfort; namely, the previously addressed flexor and extensor muscles which share a common origin at the epicondyle heads of the humerus, and the muscles which share a common insertion at the olecranon process and subsequently continue over the anconeus to eventually blend with the deep fascia of the forearm. All previously discussed functions are applicable to this alternate embodiment with the change in location, from distal to proximal.

In a fourth preferred embodiment (FIGS. 24 and 25) of a forearm-encircling sleeve device 1''' made in accordance with the present invention, the device 1''' is modified from the embodiment of FIGS. 8–14 by providing an energy-attenuating viscoelastic means 50 in the form of a single extended viscoelastic elastomer pad 58 that is positioned in force-receiving relationship with the major portion of the musculature on the dorsal (outside) of the forearm and in a position distal to the elbow joint and to the common extensor tendon origin of the lateral epicondyle of the humerus. The viscoelastic elastomer pad 58 may be in the form of a rectangle and, preferably, may have dimensions of about 4 inches long by about two inches wide. The broad area provided by the pad 58 provides a greater amount of energy-attenuating viscoelastic material in force-receiving relationship with the musculature on the dorsal side of the forearm. The fastening means 30 functions as previously stated. This embodiment represents an alternate embodiment of a sleeve intended to attenuate impact-induced shock. In particular, this embodiment is intended for industrial use, namely, chippers using pneumatic hammers, mechanics, steel erectors, etc. It is generally accepted that the majority of elbow related injuries occur at the common flexor tendon origin. It is the purpose of this embodiment to maximize the coverage of those flexor muscles thereby maximizing the shock attenuating/pressure buffer means. It should be understood that while the pad 58 has been described as positioned on the dorsal side of the forearm, it could be provided to the inside of the forearm or two such pads could be provided, such as one for the dorsal side and one for the inside of the forearm.

While the present invention has been described with respect to certain particular embodiments thereof it is apparent that numerous other forms and modifications of this invention will be obvious to those skilled in the art the appended claims and this invention generally should be construed to cover all forms and modifications that are within the true spirit and scope of the present invention.

What we claim is:

1. A forearm-encircling sleeve for attenuating the effect of impact-induced shock on the elbow joint comprising:
   a. a sleeve member and
   b. energy-attenuating viscoelastic means for attenuating impact-induced shock, said sleeve member being adapted so that said energy-attenuating viscoelastic means is placed distal to the elbow joint and to the common tendon origin of the medial and the lateral epicondyle heads of the humerus and in force-receiving relationship with forearm musculature responsible for flexion and extension of the wrist.

2. A sleeve as defined by claim 1 wherein
   said energy-attenuating viscoelastic means comprises first and second energy-attenuating viscoelastic polymer pads, said first viscoelastic polymer pad is adapted to be placed distal to the lateral epicondyle head of the humerus and in force-receiving relationship with the forearm musculature responsible for extension of the wrist and said second viscoelastic polymer pad is adapted to be placed distal to the medial epicondyle head of the humerus and in force-receiving relationship with forearm musculature responsible for flexion of the wrist.

3. A sleeve as defined by claim 1 wherein said device further comprises means for applying a counterforce to said energy-attenuating viscoelastic means.

4. A sleeve as defined by claim 3 wherein said means for applying a counterforce comprises a strap member that is adapted to overly said energy-attenuating viscoelastic means.

5. A sleeve as defined by claim 4 wherein said strap member is adapted to apply pressure directed radially inwardly over said energy-attenuating viscoelastic means.

6. A sleeve as defined by claim 1 wherein said sleeve member comprises an upper arm encircling extension.

7. A sleeve as defined by claim 1 wherein said sleeve member comprises a heat insulative material.

8. A sleeve as defined by claim 1 wherein said sleeve member is elastic and is adapted to apply pressure radially inwardly to the forearm sufficient to produce the onset of restriction of venous blood in the forearm.

9. A sleeve as defined by claim 1 wherein said energy-attenuating viscoelastic means comprises a viscoelastic polyurethane elastomer.

10. A sleeve as defined by claim 1 wherein said energy-attenuating viscoelastic means at least partially isolates the elbow joint from impact-induced shock transferred through the muscle-tendon complexes of the forearm.

11. A sleeve as defined by claim 1 wherein said energy-attenuating viscoelastic means are adapted to be placed distally of the elbow joint in the path of transmission of impact-induced shock.

12. A sleeve as defined by claim 2 wherein said energy-attenuating viscoelastic means further comprises:

a third viscoelastic polymer pad that is adapted to be placed proximal of the elbow joint and in force-receiving relationship with the insertion of the triceps brachii muscle of the upper arm.

13. A sleeve as defined by claim 1 wherein said energy-attenuating viscoelastic means comprises:

a viscoelastic polymer pad that is adapted to be placed distal of the elbow joint and to the common extensor tendon origin of the lateral epicondyle of the humerus and in force-receiving relationship with the musculature of the forearm on the dorsal side of the forearm.

14. A sleeve as defined by claim 1 wherein said energy-attenuating viscoelastic means comprises:

a viscoelastic polymer pad that is adapted to be placed distal of the elbow joint and to the common flexor tendon origin of the medial epicondyle of the humerus and in force-receiving relationship with the musculature of the forearm on the inside of the forearm.

15. A forearm-encircling sleeve for attenuating the effect of impact-induced shock on the elbow joint comprising:

a. a sleeve member and b. energy-attenuating viscoelastic means for attenuating impact-induced shock, said sleeve member being adapted so that said energy-attenuating viscoelastic means is placed distally of the elbow joint and in the path of transmission of impact-induced shock.

16. A forearm-encircling sleeve for attenuating the effect of impact-induced shock on the elbowjoint comprising:

a. a sleeve member and b. energy-attenuating viscoelastic means for attenuating impact-induced shock, said sleeve member being adapted to place said energy-attenuating viscoelastic means distally to the elbow joint to at least partially isolate the elbow joint from impact-induced shock transferred through the muscle-tendon complexes of the forearm.

* * * * *